United States Patent [19]

Weyer et al.

[11] 4,282,239

[45] Aug. 4, 1981

[54] SULFONYL UREAS AND PHARMACEUTICAL PREPARATIONS THEREOF

[75] Inventors: Rudi Weyer, Kelkheim; Volker Hitzel, Hofheim am Taunus; Karl Geisen, Frankfurt am Main; Günter Regitz, Bad Soden am Taunus, all of Fed. Rep. of Germany

[73] Assignee: Hoechst Aktiengesellschaft, Frankfurt am Main, Fed. Rep. of Germany

[21] Appl. No.: 51,548

[22] Filed: Jun. 25, 1979

[30] Foreign Application Priority Data

Jun. 27, 1978 [DE] Fed. Rep. of Germany ....... 2828079

[51] Int. Cl.³ ................. A61K 31/40; C07D 207/12
[52] U.S. Cl. .............................. 424/274; 260/325 PH; 424/258; 546/141
[58] Field of Search ................ 260/325 PH; 424/274

[56] References Cited

U.S. PATENT DOCUMENTS

| | | | |
|---|---|---|---|
| 3,510,496 | 5/1970 | Aumuller et al. | 260/325 PH |
| 3,705,151 | 12/1972 | Weber et al. | 424/275 |
| 3,810,914 | 5/1974 | Beregi et al. | 260/326.1 |
| 3,980,655 | 9/1976 | Kunstmann et al. | 546/141 |
| 4,065,456 | 12/1977 | Nakagawa et al. | 546/141 |
| 4,129,729 | 12/1978 | Houbion | 260/325 PH |

FOREIGN PATENT DOCUMENTS

| | | |
|---|---|---|
| 803321 | 2/1974 | Belgium . |
| 1445774 | 1/1969 | Fed. Rep. of Germany . |
| 1670700 | 11/1970 | Fed. Rep. of Germany . |
| 1670660 | 12/1970 | Fed. Rep. of Germany . |
| 2000339 | 7/1971 | Fed. Rep. of Germany . |
| 2157607 | 5/1973 | Fed. Rep. of Germany . |
| 1618389 | 7/1974 | Fed. Rep. of Germany . |
| 1528139 | 4/1968 | France . |
| 2085759 | 12/1971 | France . |

*Primary Examiner*—Donald G. Daus
*Assistant Examiner*—M. C. Eakin
*Attorney, Agent, or Firm*—Curtis, Morris & Safford

[57] ABSTRACT

Sulfonylureas of the formula

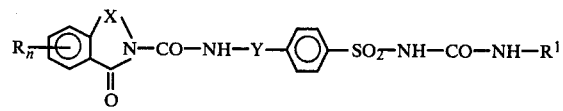

in which n, R, R¹, X and Y have the indicated meanings and the physiologically acceptable salts thereof, pharmaceutical preparations on the basis of said compounds and their use in the treatment of diabetes.

8 Claims, No Drawings

SULFONYL UREAS AND PHARMACEUTICAL PREPARATIONS THEREOF

The invention relates to sulfonylureas of the formula

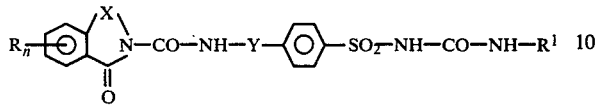

which, as such or in the form of their physiologically acceptable salts, possess blood sugar-lowering properties and are distinguished by a pronounced and long-lasting lowering of the blood sugar level so that they can be used as medicaments.

In the formula, the symbols have the following meanings:

n: 1 or 2

R: hydrogen, alkyl with 1 to 4 carbon atoms, alkoxy with 1 to 4 carbon atoms or halogen which, with n being 2, may be identical or different, X: a —CH$_2$—, —CH$_2$—CH$_2$— or $$\begin{array}{c} CH_3 \\ | \\ -CH- \end{array}$$

group,

Y: alkylene with 2-3 C atoms,

R$^1$: alkyl of 2 to 8 C atoms, cycloalkyl, alkylcycloalkyl, dialkylcycloalkyl, cycloalkylalkyl, cycloalkenyl or alkylcycloalkenyl, in each case with 4–9 C atoms, methylcyclopentylmethyl, cyclohexenylmethyl, chlorocyclohexyl, methoxycyclohexyl, bicycloheptyl, bicycloheptenyl, bicycloheptylmethyl, bicycloheptenylmethyl, bicyclooctyl, nortricyclyl, adamantyl or benzyl.

In the general formula, R preferably denotes hydrogen, methyl and halogen, especially chlorine. Preferred disubstitution products are the dichloro-compounds. The particularly preferred meaning of R is hydrogen. X preferably denotes the —CH$_2$— group and Y preferably denotes —CH$_2$—CH$_2$— or $$\begin{array}{c} -CH-CH_2-, \\ | \\ CH_3 \end{array}$$

the former being particularly preferred. R$^1$ is preferably butyl, isobutyl, isobutyl, methylcyclopentyl, cyclopentylmethyl, or cyclohexyl; cyclohexyl and 3-methylcyclopentyl are particularly preferred.

The invention further relates to processes for the manufacture of these sulfonylureas, pharmaceutical preparations which contain these or consist of these compounds, and their use for the treatment of diabetes.

The processes of manufacture are characterized in that (a) benzenesulfonyl-isocyanates, -carbamic acid esters, -thiolcarbamic acid esters, -ureas, -semicarbazides or -semicarbazones, which are substituted in the 4-position by the group

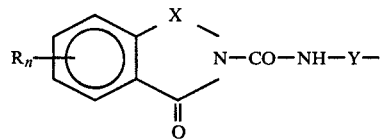

are reacted with an amine R$^1$-NH$_2$ or its salts, or sulfonamides of the formula

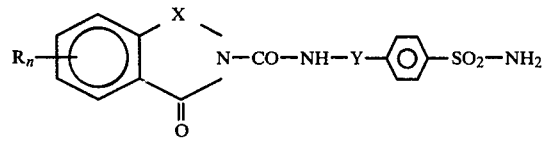

or their salts are reacted with R$^1$-substituted isocyanates, carbamic acid esters, thiolcarbamic acid esters, carbamic acid halides or ureas, (b) benzenesulfonyl-isourea-ethers, -isothiourea-ethers, parabanic acids or -haloformamidines substituted by the group

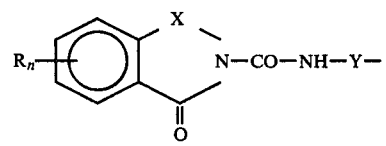

or benzenesulfonylureas substituted by the group

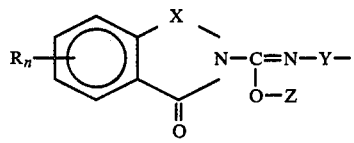

in which Z denotes alkyl having 1 or 2 carbon atoms are caused to undergo scission, (c) in benzenesulfonylthioureas substituted by

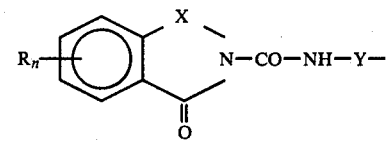

the sulfur atom is replaced by oxygen, (d) corresponding benzenesulfinyl-ureas or -sulfenylureas are oxidized, (e) the radical

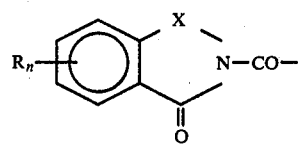

is introduced, if appropriate stepwise, into benzenesulfonylureas of the formula

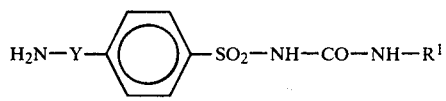

or (f) correspondingly substituted benzenesulfonyl halides are reacted with $R^1$-substituted ureas or their alkali metal salts or correspondingly substituted benzenesulfinic acid halides or, in the presence of acid condensation agents, also correspondingly substituted sulfinic acids or their alkali metal salts, are reacted with N-$R^1$-N'-hydroxy-urea and, if desired, the reaction products are treated with alkaline agents in order to form the salts.

The benzenesulfonyl-carbamic acid esters and -thiolcarbamic acid esters which have been mentioned can contain an alkyl radical or an aryl radical, or even a heterocyclic radical, in the alcohol component. Since this radical is split off during the reaction, its chemical structure has no influence on the character of the end product and can therefore be varied within wide limits. The same is true of the N-$R^1$-substituted carbamic acid esters and the corresponding thiolcarbamic acid esters.

Suitable carbamic acid halides are above all the chlorides.

The benzenesulfonylureas which may be used as starting materials for the process can be unsubstituted, monosubstituted or, in particular, disubstituted on the side of the urea molecule opposite from that carrying the sulfonyl group. Since these substituents are split off during the reaction with amines, their character can be varied within wide limits. In addition to alkyl-, aryl-, acyl- or heterocyclyl-substituted benzenesulfonylureas it is also possible to use benzenesulfonylcarbamoylimidazoles and similar compounds or bisbenzenesulfonylureas which on one of the nitrogen atoms can carry a further substituent, for example methyl. For example, such bis(benzenesulfonyl)-ureas or N-benzenesulfonyl-N'acylureas can be treated with $R^1$-substituted amines and the resulting salts can be heated to elevated temperatures, especially to temperatures above 100° C.

Furthermore, it is possible to start from $R^1$-substituted ureas, or from those $R^1$-substituted ureas which are additionally monosubstituted or, in particular, disubstituted at the free nitrogen atom, and to react these with benzenesulfonamides substituted by

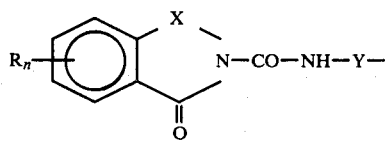

in the 4-position. Examples of possible starting materials of this type are N-cyclohexyl-urea, the corresponding N'-acetyl-, N'-nitro-, N'-cyclohexyl-, N',N'-diphenyl-, (it being possible for the two phenyl radicals also to be substituted and to be bonded to one another either directly or via a bridge member such s —$CH_2$—, —NH—, —O— or —S—), N'-methyl-N'-phenyl- and N',N'-dicyclohexylureas as well as cyclohexyl-carbamoyl-imidazoles, -pyrazoles or -triazoles, and those of the compounds mentioned which instead of cyclohexyl carry some other substituent falling within the range of definition of $R^1$.

The scission of the benzenesulfonylparabanic acids, -isourea-ethers, -isothiourea-ethers or -haloformamidines mentioned as starting materials in process (b) and of the benzenesulfonylureas mentioned is advantageously effected by alkaline hydrolysis. Isourea-ethers can also be very successfully subjected to scission in an acid medium.

The replacement of the sulfur atom in the urea grouping of correspondingly substituted benzenesulfonyl-thioureas by an oxygen atom can be effected in a known manner, for example with the aid of oxides or salts of heavy metals or by using oxidizing agents, such as hydrogen peroxide, sodium peroxide, nitrous acid or permanganates. The thioureas can also be desulfurized by treatment with phosgene or phosphorus pentachloride. Chloroformamidines or carbodiimides obtained as intermediates can be converted into the benzenesulfonylureas by suitable measures such as hydrolysis or addition reaction with water.

The oxidation of benzenesulfinylureas and benzenesulfenylureas is carried out in accordance with a method which is in itself known, preferably with oxidizing agents such as permanganate or hydrogen peroxide.

The acylation of the sulfonylureas according to process (e) can be carried out with reactive derivatives of the acid

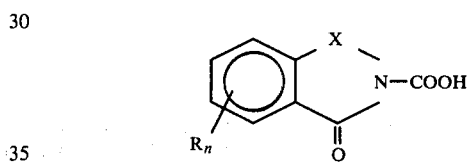

such as, for example, halides.

Suitable sulfonyl halides and sulfinyl halides for use in process (f) are in particular the chlorides. The acid condensation agent employed can be, for example, thionyl chloride or polyphosphoric acid.

The physiologically acceptable salts are manufactured in accordance with methods which are in themselves known. In particular, alkali metal and alkaline earth metal hydroxides, carbonates or bicarbonates, and physiologically tolerated organic bases, are suitable for forming salts.

The embodiments of the process according to the invention can in general be varied substantially in respect of the reaction conditions and be suited to the particular circumstances. For example, the reactions can be carried out in the absence or presence of solvents, at room temperature or at an elevated temperature.

Depending on the character of the starting materials, one or other of the processes described can, in some cases, give a desired individual benzenesulfonylurea only in low yields, or can be unsuitable for its synthesis. In such relatively rarely occuring cases it presents no difficulties to an expert to synthesize the desired product by another of the methods described. The method as described in Example 1 is the best one, the desired benzenesulfonylureas are obtained in good yields.

The compounds obtained can be purified by dissolution and reprecipitation and/or recrystallization. Alternatively, purification is also possible by liberating the substance from a crystalline (alkali metal) salt by means of a suitable solvent.

The compounds according to the invention are distinguished by valuable pharmacological properties, especially blood sugar-lowering properties. They are therefore suitable for use as medicaments, especially as antidiabetics.

The blood sugar-lowering action of the benzenesulfonylureas described can be ascertained by feeding them as the free compounds, or in the form of the sodium salts to rabbits which have received normal nutrition, and determining the blood sugar value by the known Hagedorn-Jensen method, or by means of an auto-analyzer, over a fairly long period of time.

For routine determination of the blood sugar lowering effect doses of 10 mg, 2 mg or 0.4 mg per kilogram of active substance are given to the test animals according to known methods.

The following compounds I to IV were administered to rabbits in doses of 0.4 mg/kg and the blood sugar values were determined by means of an auto-analyzer over a fairly long period of time. The lowering of the blood sugar, thus measured, is shown in the table below in % after 1, 3, 6, 24, 72, 96, 120 and 144 hours.

I   N-(4-[2-(1-oxo-isoindoline-2-carboxamido)-ethyl]benzenesulfonyl)-N'-butyl-urea II   N-(4-[2-(1-oxo-isoindoline-2-carboxamido)-ethyl]-benzenesulfonyl)-N'-cyclohexyl-urea III   N-(4-[2-(1-oxo-isoindoline-2-carboxamido)-ethyl]-benzenesulfonyl)-N'-3-methyl-cyclopentyl-urea IV   N-(4-[2-(1-oxo-isoindoline-2-carboxamido)-ethyl]-benzenesulfonyl)-N'-2,5-endomethylene-cyclohex-3-enyl-methyl-urea

TABLE

| Compound | Lowering of blood sugar in rabbits after oral administration of 0.4 mg/kg, in % after ... hours | | | | | | | | |
|---|---|---|---|---|---|---|---|---|---|
| | 1 | 3 | 6 | 24 | 48 | 72 | 96 | 120 | 144 hrs |
| I | 6 | 14 | 20 | 28 | 8 | 0 | | | |
| II | 33 | 35 | 47 | 48 | 54 | 40 | 0 | | |
| III | 20 | 27 | 44 | 50 | 68 | 64 | 60 | 32 | 0 |
| IV | 21 | 32 | 28 | 34 | 0 | | | | |

The acylureido-alkylbenzenesulfonylureas according to the invention are distinguished by a pronounced and long-lasting blood sugar-lowering action.

The properties of the compounds make it possible to manage with such low doses in the therapy of diabetes mellitus that the preparation merely re-normalizes the reduced response capacity of the pancreas to an increased blood sugar level. Furthermore, they are well tolerated.

Benzenesulfonylureas containing a ureidoalkyl radical have already been described on several occasions DE-PS No. 1,443,911, DE-AS No. 1,670,700, DE-PS No. 1,618,389 and DE-AS No. 2,238,870). Benzenesulfonylureas containing an acylureidoalkyl radical were not previously known and it was not to be expected that they would be distinguished by the advantageous properties mentioned above.

The sulfonylureas described are preferentially intended for the manufacture of orally administrable preparations for the treatment of patients suffering from or afflicted with diabetes mellitus. They can be administered as such or in the form of their salts or in the presence of material which lead to salt formation. For example, alkaline agents, such as alkali metal or alkaline earth metal hydroxides, carbonates or bicarbonates may be employed for forming salts. In addition to the sulfonylurea or its salt, the preparations can also contain other active compounds.

Suitable medicinal preparations are preferably tablets which in addition to the products of the process contain the customary excipients and auxiliaries such as talc, starch, lactose or magnesium stearate. It can be advantageous to use the active substance(s) in ground or finely precipitated form or as a mixture thereof. A preparation which contains the described benzenesulfonylureas as the active compound, for example a tablet or a powder, with or without additives, is advantageously converted to a suitably dosed form. The dose to be selected in this context is such as to suit the activity of the benzenesulfonylurea employed and to suit the desired effect. Advantageously, the dosage per unit is about 0.1 to 10 mg, preferably 0.5 to 2 mg, but dosage units above or below this, which may have to be divided before administration or of which several may have to be taken, can also be used.

The examples which follow show some of the numerous process variants which can be used for the synthesis of the sulfonylureas according to the invention. They are, however, not intended to imply a limitation of the subject of the invention.

EXAMPLE 1

N-(4-[2-(1-Oxo-isoindoline-2-carboxamido)-ethyl]-benzenesulfonyl)-N'-cyclohexyl-urea 7.2 g of 4-(2-[1-oxo-isoindoline-2-carboxamido]-ethyl)benzenesulfonamide (melting point 236°–238° C., prepared by reaction of 1-oxo-isoindoline-2-(N-2-phenylethyl)-carboxamide [melting point 146°–148° C., prepared by heating 1-oxo-isoindoline and phenylethyl isocyanate at 150° C. or by heating the two compounds in the presence of an inert solvent at 100° C.] with chlorosulfonic acid at a temperature of about 40° C., and reaction of the resulting sulfochloride with ammonia in known manner), in 300 ml of acetone are heated to the boil with 5.5 g of ground potassium carbonate for several hours, whilst stirring. 2.5 g of cyclohexyl isocyanate are then added and the mixture is stirred for a further 5 hours at the boil. After cooling, the potassium salt of the sulfonylurea formed is filtered off and dissolved in water, the solution is filtered and the filtrate is acidified with dilute hydrochloric acid. The N-(4-[2-(1-oxo-isoindoline-2-carboxamido)ethyl]-benzene-sulfonyl)-N'-cyclohexyl-urea which has precipitated is filtered off and recrystallized from dilute acetone. The product melts at 214°–216° C.

The following compounds are obtained analogously:
N-(4-[2-(1-Oxo-isoindoline-2-carboxamido)-ethyl]-benzene-sulfonyl)N'-butyl urea, melting at 188°–190° C. (after crystallization from dilute acetone).
N-(4-[2-(1-Oxo-isoindoline-2-carboxamido)-ethyl]-benzenesulfonyl)-N'-hexyl urea, melting at 179°–181° C. (after crystallization from dioxane).
N-(4-[2-(1-Oxo-isoindoline-2-carboxamido)-ethyl]-benzenesulfonyl)-N'-ethyl urea, melting at 209°–211° C. (after crystallization from dilute acetone).
N-(4-[2-(1-Oxo-isoindoline-2-carboxamido)-ethyl]-benzenesulfonyl)-N'-4-methyl-cyclohexyl-urea, melting at 228°–230° C. (after crystallization from dilute acetone).
N-(4-[2-(1-Oxo-isoindoline-2-carboxamido)-ethyl]-benzenesulfonyl)N'-cyclohex-3-enyl-urea, melting at 199°–201° C. (after crystallization from aqueous acetone).

N-(4-[2-(1-Oxo-isoindoline-2-carboxamido)-ethyl]-benzenesulfonyl)-N'-2,5-endomethylene-cyclohexyl-urea, melting at 203°–205° C. (after crrystallization from dioxane).

N-(4-[2-(1-Oxo-isoindoline-2-carboxamido)-ethyl]-benzenesulfonyl)-N'-4,4-dimethyl-cyclohexyl-urea, melting at 213°–215° C. (after crystallization from dilute acetone).

N-(4-[2-(1-Oxo-isoindoline-2-carboxamido)-ethyl]-benzenesulfonyl)-N'-cyclooctyl-urea, melting at 178°–180° C. (after crystallization from dilute acetone).

N-(4-[2-(1-Oxo-isoindoline-2-carboxamido)-ethyl]-benzenesulfonyl)-N'-benzyl-urea, melting at 204°–206° C. (after crystallization from dioxane).

N-(4-[2-(1-Oxo-isoindoline-2-carboxamido)-ethyl]-benzenesulfonyl)-N'-2,5-endomethylene-cyclohex-3-enyl-urea.

N-(4-[2-(1-Oxo-isoindoline-2-carboxamido)-ethyl]-benzenesulfonyl)-N'-(4-isopropyl-cyclohexyl)-urea, melting at 213°–215° C. (after crystallization from dilute acetone).

N-(4-[2-(1-Oxo-isoindoline-2-carboxamido)-ethyl]-benzenesulfonyl)-N'-cyclohex-3-enylmethyl-urea, melting at 203°–205° C. (after crystallization from dilute acetone).

N-(4-[2-(1-Oxo-isoindoline-2-carboxamido)-ethyl]-benzenesulfonyl)-N'-isobutyl-urea, melting at 196°–198° C. (after crystallization from dilute acetone).

N-(4-[2-(1-Oxo-isoindoline-2-carboxamido)-ethyl]-benzenesulfonyl)-N'-propyl-urea, melting at 200°–202° C. (after crystallization from dilute acetone).

N-(4-[2-(1-Oxo-isoindoline-2-carboxamido)-ethyl]-benzenesulfonyl)-N'-(2,5-endomethylene-cyclohexylmethyl)-urea, melting at 203°–205° C. (after crystallization from dilute acetone).

N-(4-[2-(1-Oxo-isoindoline-2-carboxamido)-ethyl]-benzenesulfonyl)-N'-(4-methyl-cyclohex-3-enyl)-urea, melting at 211°–213° C. (after crystallization from dioxane).

Analogously, 4-(2-[5-methyl-1-oxo-isoindoline-2-carboxamido)-ethyl]-benzenesulfonamide (melting point 243°–246° C., prepared from 5-methyl-1-oxo-isoindoline-2-(N-2-phenylethyl)-carboxamide [melting point 159°–162° C., prepared from 5-methyl-1-oxo-isoindoline and phenylethyl isocyanate] and chlorosulfonic acid, followed by reaction of the sulfochloride with ammonia) gives N-(4-[2-(5-methyl-1-oxo-isoindoline-2-carboxamido)-ethyl]-benzenesulfonyl)N'-cyclohexyl-urea, melting at 216°–218° C. (after crystallization from dilute dioxane).

Analogously, 4-(2-[5-chloro-1-oxo-isoindoline-2-carboxamido)-ethyl]-benzenesulfonamide melting point 245°–247° C., prepared from 5-chloro-1-oxo-isoindoline-2-(N-2-phenylethyl)-carboxamide [melting point 160°–162° C., prepared from 5-chloro-1-oxo-isoindoline and phenylethyl isocyanate] and chlorosulfonic acid, followed by reaction of the sulfochloride with ammonia) gives N-(4-[2-(5-chloro-1-oxo-isoindoline-2-carboxamido)-ethyl]-benzenesulfonyl)-N'-cyclohexyl-urea, melting at 237°–239° C. (after crystallization from aceton/dioxane) and N-(4-[2-(5-chloro-1-oxo-isoindoline-2-carboxamido)-ethyl]-benzenesulfonyl)-N'-butyl-urea, melting at 215°–217° C. (after crystallization from dilute dioxane).

Analogously, 4-(2-[1-oxo-isoindoline-2-carboxamido)propyl]-benzenesulfonamide (melting point 183°–185° C., prepared by reaction of 1-oxo-isoindoline-2-(N-2-phenylpropyl)-carboxamide [melting point 126°–128° C., prepared from 1-oxo-isoindoline and 2-phenylpropyl isocyanate] with chlorosulfonic acid, followed by reaction of the resulting sulfochloride with ammonia) gives N-(4-[2-(1-oxo-isoindoline-2-carboxamido)-propyl]-benzenesulfonyl)-N'-cyclohexyl-urea, melting at 197°–198° C. (after crystallization from ethanol.

Analogously, 4-(2-[6-methyl-1-oxo-isoindoline-2-carboxamido)-ethyl]-benzenesulfonamide (melting point 227°–230° C. prepared from 6-methyl-1-oxo-isoindoline-2-(N-2-phenylethyl)-carboxamide [melting point 143°–144° C., prepared from 6-methyl-1-oxo-isoindoline and phenylethyl isocyanate] and chlorosulfonic acid, followed by reaction of the sulfochloride with ammonia) gives N-(4-[2-(6-methyl-1-oxo-isoindoline-2-carboxamido)-ethyl]-benzenesulfonyl)-N'-cyclohexyl-urea, melting at 212°–214° C. (after crystallization from dilute dioxane) and N-(4-[2-(6-methyl-1-oxo-isoindoline-2-carboxamido)-ethyl]benzenesulfonyl)-N'-butyl-urea melting at 169°–171° C., (after crystallization from dilute dioxane).

Analogously, 4-(2-[6-chloro-1-oxo-isoindoline-2-carboxamido)-ethyl]-benzenesulfonamide (melting point 223°–226° C., prepared from 6-chloro-1-oxo-isoindoline-2-(N-2-phenylethyl)-carboxamide [melting point 169°–171° C., prepared from 6-chloro-1-oxo-isoindoline and phenylethyl isocyanate] and chlorosulfonic acid, followed by reaction of the sulfochloride with ammonia) gives N-(4-[2-(6-chloro-1-oxo-isoindoline-2-carboxamido)-ethyl]-benzenesulfonyl)-N'-cyclohexyl-urea, melting at 230°–232° C. (after crystallization from dilute dioxane) and N-(4-[2-(6-chloro-1-oxo-isoindoline-2-carboxamido)-ethyl]benzenesulfonyl)-N'-butyl-urea melting at 208°–210° C., (after crystallization from dilute dioxane).

Analogously, 4-(2-[4,6-dichloro-1-oxo-isoindoline-2-carboxamido)-ethyl]-benzenesulfonamide (melting point 204°–206° C., prepared from 4,6-dichloro-1-oxo-isoindoline-2-(N-2-phenylethyl)-carboxamide [melting point 137°–139° C., prepared from 4,6-dichloro-1-oxo-isoindoline (melting point 282°–284° C.] and phenylethyl isocyanate] and chlorosulfonic acid, followed by reaction of the sulfochloride with ammonia) gives N-(4-[2-(4,6-dichloro-1-oxo-isoindoline-2-carboxamido)-ethyl]-benzenesulfonyl)-N'-cyclohexyl-urea, melting at 249°–251° C. (after crystallization from dioxane) and N-(4-[2-(4,6-dichloro-1-oxo-isoindoline-2-carboxamido)-ethyl]-benzenesulfonyl)-N'-butyl-urea melting at 190°–192° C. (after crystallization from dilute dioxane).

Analogously, 4-(2-[3-methyl-1-oxo-isoindoline-2-carboxamido)-ethyl]-benzenesulfonamide (melting point 193°–195° C., prepared from 3-methyl-1-oxo-isoinodoline-2-(N-2-phenylethyl)-carboxamide [melting point 80°–82° C., prepared from 3-methyl-1-oxo-isoindoline and phenylethyl isocyanate] and chlorosulfonic acid, followed by reaction of the sulfochloride with ammonia) gives N-(4-[2-(3-methyl-1-oxo-isoindoline-2-carboxamido)-ethyl]-benzenesulfonyl)-N'-cyclohexyl-urea, melting at 124°–125° C. (after crystallization from ethyl acetate), N-(4-[2-(3-methyl-1-oxo-isoindoline-2-carboxamido)-ethyl]-benzenesulfonyl)-N'-butyl-urea, melting at 164°–165° C. (after crystallization from ethanol/ethyl acetate, and N-(4-[2-(3-methyl-1-oxo-isoindoline-2-carboxamido)-ethyl]-benzenesulfonyl)-N'-(4-methyl-cyclohexyl)-urea melting at 212°–214° C., (after crystallization from ethanol/dimethyl formamide).

EXAMPLE 2

N-(4-[2-(1-Oxo-1,2,3,4-tetrahydro-isoquinoline-2-carboxamido)-ethyl]-benzenesulfonyl)-N'-cyclohexyl-urea 5.5 g of 4-(2-[1-oxo-1,2,3,4-tetrahydroisoquinoline-2-carboxamido]-ethyl)-benzenesulfonamide (melting point 197°–198° C., prepared from 1-oxo-1,2,3,4-tetrahydroisoquinoline-2-(N-2-phenylethyl)-carboxamide [melting point 98°–99° C., prepared from 1-oxo-1,2,3,4-tetrahydro-isoquinoline and 2-phenylethyl isocyanate] and chlorosulfonic acid, with subsequent reaction of the sulfochloride with ammonia) are suspended in 75 ml of acetone and 7.5 ml of 2 N sodium hydroxide solution and the mixture is cooled to 0°–5° C. 2.15 g of cyclohexyl isocyanate in 10 ml of acetone are added dropwise, whilst stirring, and the mixture is then stirred for one hour whilst cooling with ice and for three hours at room temperature. The precipitate is dissolved by adding water. After removing the acetone in vacuo, the aqueous solution which remains is acidified with dilute hydrochloric acid. The N-(4-[2-(1-oxo-1,2,3,4-tetrahydro-isoquinoline-2-carboxamido)-ethyl]-benzenesulfonyl)-N'-cyclohexyl-urea which has precipitated is filtered off with suction, reprecipitated once from dilute ammonia solution by means of dilute hydrochloride acid, filtered off with suction, dried and recrystallized from ethanol. The product thus obtained melts at 197°–199° C.

The following compounds are obtained analogously:

N-(4-[2-(1-Oxo-1,2,3,4-tetrahydro-isoquinoline-2-carboxamido)-ethyl]-benzenesulfonyl)-N'-4-methyl-cyclohexyl-urea, melting at 203°–205° C. (after crystallization from ethanol).

N-(4-[2-(1-Oxo-1,2,3,4-tetrahydro-isoquinoline-2-carboxamido)-ethyl]-benzenesulfonyl)-N'-butyl-urea, melting at 144°–146° C. (after crystallization from ethanol).

N-(4-[2-(1-Oxo-1,2,3,4-tetrahydro-isoquinoline-2-carboxamido)-ethyl]-benzenesulfonyl)-N'-isobutyl-urea, melting at 167°–168° C. (after crystallization from ethanol).

N-(4-[2-(1-Oxo-1,2,3,4-tetrahydro-isoquinoline-2-carboxamido)-ethyl]-benzenesulfonyl)-N'-4-ethyl-cyclohexyl-urea, melting at 168°–170° C. (after crystallization from ethanol).

EXAMPLE 3

N-(4-[2-(1-Oxo-isoindoline-2-carboxamido)-ethyl]-benzenesulfonyl)-N'-cyclohexyl-urea 4.2 g of N-(4-[2-(1-oxo-isoindoline-2-carboxamido)-ethyl]-benzenesulfonyl)-carbamic acid methyl ester (melting point 215°–217° C., prepared from 4-(2-[1-oxo-isoindoline-2-carboxamido]-ethyl)-benzenesulfonamide and methyl chloroformate) are dissolved in 100 ml of dioxane at 50° C. and 1 g of cyclohexylamine is added. The cyclohexylamine salt of the urethane, which precipitates, dissolves slowly on boiling under reflux for one hour. The mixture is concentrated to ⅓ of its volume and the residual solution is poured onto dilute hydrochloric acid. N-(4-[2-(1-Oxo-isoindoline-2-carboxamido)-ethyl]-benzenesulfonyl)-N'-cyclohexyl-urea, which is obtained in good yield, is filtered off and recrystallized from aqueous acetone. It melts at 214°–216° C.

The following compounds are obtained analogously:

N-(4-[2-(1-Oxo-isoindoline-2-carboxamido)-ethyl]-benzenesulfonyl)-N'-2,5-endomethylene-cyclohex-3-enyl-methyl-urea, melting at 204°–206° C. (after crystallization from aqueous acetone), N-(4-[2-(1-oxo-isoindoline-2-carboxamido)-ethyl]-benzenesulfonyl)-N'-cyclopentyl-urea, melting at 210°–212° C. (after crystallization from aqueous acetone), N-(4-[2-(1-oxo-isoindoline-2-carboxamido)-ethyl]-benzenesulfonyl)-N'-3-methyl-cyclopentyl-urea, melting at 194°–196° C. (after crystallization from aqueous acetone), N-(4-[2-(1-oxo-isoindoline-2-carboxamido)-ethyl]-benzenesulfonyl)-N'-4-isopropyl-cyclohexyl-urea, melting at 213°–215° C. (after crystallization from aqueous acetone), N-(4-[2-(1-oxo-isoindoline-2-carboxamido)-ethyl]-benzenesulfonyl)-N'-4-chlorocyclohexyl-urea, melting at 209°–211° C. (after crystallization from aqueous acetone), N-(4-[2-(1-oxo-isoindoline-2-carboxamido)-ethyl]-benzenesulfonyl)-N'-cyclohex-2-enyl-methyl-urea, melting at 203°–205° C. (after crystallization from aqueous acetone), N-(4-[2-(1-oxo-isoindoline-2-carboxamido)-ethyl]-benzenesulfonyl)-N'-cyclopentylmethyl-urea, melting at 212°–214° C. (after crystallization from dilute tetrahydrofuran), N-(4-[2-(1-oxo-isoindoline-2-carboxamido)-ethyl]-benzenesulfonyl)-N'-(3-ethylcyclopentyl)-urea, melting at 192°–194° C. (after crystallization from dilute tetrahydrofurane), N-(4-[2-(1-oxo-isoindoline-2-carboxamido)-ethyl]-benzenesulfonyl)-N'-nortricyclyl-urea, melting at 226°–228° C. (after crystallization from methanol/dioxane), N-(4-[2-(1-oxo-isoindoline-2-carboxamido)-ethyl]-benzenesulfonyl)-N'-sec.butyl-urea, melting at 187°–189° C. (after crystallization from methanol), N-(4-[2-(1-oxo-isoindoline-2-carboxamido)-ethyl]-benzenesulfonyl)-N'-(3,4-dimethyl-cyclohexyl)-urea, melting at 201°–203° C. (after crystallization from dilute methanol), N-(4-[2-(1-oxo-isoindoline-2-carboxamido)-ethyl]-benzenesulfonyl)-N'-cyclohept-2-enyl-urea, melting at 196°–198° C. (after crystallization from methanol/dioxane), N-(4-[2-(1-oxo-isoindoline-2-carboxamido)-ethyl]-benzenesulfonyl)-N'-(4-methoxy-cyclohexyl)-urea, melting at 183°–185° C. (after crystallization from methanol), N-(4-[2-(1-oxo-isoindoline-2-carboxamido)-ethyl]-benzenesulfonyl)-N'-cyclopent-2-enyl-urea, melting at 196°–198° C. (after crystallization from methanol/dioxane), N-(4-[2-(1-oxo-isoindoline-2-carboxamido)-ethyl]-benzenesulfonyl)-N'-cyclobutyl-urea, melting at 206°–208° C. (after crystallization from dilute acetone), N-(4-[2-(1-oxo-isoindoline-2-carboxamido)-ethyl]-benzenesulfonyl)-N'-(3-methyl-cyclopentylmethyl)-urea, melting at 192°–194° C. (after crystallization from methanol/water).

EXAMPLE 4

N-(4-[2-(1-Oxo-1,2,3,4-tetrahydro-isoquinoline-2-carboxamido)-ethyl]-benzenesulfonyl)-N'-2,5-endomethylene-cyclohexyl-urea 2.08 g of N-(4-[2-(1-oxo-1,2,3,4-tetrahydro-isoquinoline-2-carboxamido)-ethyl]-benzenesulfonyl)-urea (melting point 200°–201° C., prepared from 4-[2-(1-oxo-1,2,3,4-tetrahydro-isoquinoline-2-carboxyamido)-ethyl]-benzenesulfonamide and potassium cyanate) in 25 ml of dioxane are refluxed for 1 hour whilst stirring together with 1.47 g of 2,5-endomethylene-cyclohexylamine hydrochloride and 0.5 g of triethylamine. After cooling, the mixture is concentrated under reduced pressure, the residue is taken up in water, filtered and acidified with 2 N hydrochloric acid. The precipitate is filtered off with suction, reprecipitated from dilute ammonia solution by means of dilute hydrochloric acid, filtered off with suction and recrystallized from ethanol. The N-(4-[2-(1-oxo-1,2,3,4-tetrahydro-isoquinoline-2-carboxamido)-ethyl]-benzenesulfonyl)-N'-2,5-endomethylene-cyclohexyl-urea melts at 191°–193° C.

EXAMPLE 5

N-(4-[2-(1-Oxo-isoindoline-2-carboxamido)-ethyl]-benzenesulfonyl)-N'-cyclohexyl-urea 0.3 g of mercury oxide is added to 0.3 g of N-(4-[2-(1-oxo-isoindoline-2-carboxamido)-ethyl]-benzenesulfonyl)-N'-cyclohexyl-thiourea (melting point 194°–196° C., prepared from 4-[2-(1-oxo-isoindoline-2-carboxamido)-ethyl]-benzenesulfonamide and cyclohexyl mustard oil) in a mixture of 50 ml of water and 50 ml of methanol and the whole is stirred for 3 hours at 40°–45° C. The precipitated mercury sulfide is filtered off with suction, the filtrate is concentrated under reduced pressure, the residue is treated with very dilute ammonia, filtered and the filtrate is acidified with dilute hydrochloric acid. The precipitated N-(4-[2-(1-oxo-isoindoline-2-carboxamido)-ethyl]-benzenesulfonyl)-N'-2,5-cyclohexyl-urea is recrystallized from dilute acetone and melts at 211°–213° C. The mixed melting point with the compound obtained according to Example 1 is without depression.

EXAMPLE 6

N-(4-[2-(1-Oxo-isoindoline-2-carboxamido)-ethyl]benzenesulfonyl)-N'-cyclohexyl-urea 0.5 g of N-(4-[2-(1-oxo-isoindoline-2-carboxamido)-ethyl]-benzenesulfonyl)-N'-cyclohexyl-isourea methyl ether (melting point 180°–182° C., prepared from 4-[2-(1-oxo-isoindoline-2-carboxamido)-ethyl]-benzenesulfonyl)-N'-cyclohexyl-thiourea by desulfurization with mercury oxide in methanol at 40° C.) in 5 ml of dioxane is heated for a few minutes on the steam bath together with 2 ml of concentrated hydrochloric acid. Water and ice are added and the precipitate is filtered off with suction. After recrystallization the N-(4-[2-(1-oxo-isoindoline-2-carboxamido)-ethyl]-benzenesulfonyl)-N'-cyclohexyl-urea melts at 214°–216° C.

In analogous manner, N-(4-[2-(1-oxo-isoindoline-2-carboxamido)-ethyl]-benzenesulfonyl)-N'-cyclohexyl-isothiourea methyl ether (melting point 149°–151° C., prepared from N-(4-[2-(1-oxo-isoindoline-2-carboxamido)-ethyl]-benzenesulfonyl)-N'-cyclohexyl-urea and methyl iodide in dioxane) by a short heating with sodium hydroxide solution in dioxane to 50° C. gives N-(4-[2-(1-Oxo-isoindoline-2-carboxamido)-ethyl]-benzenesulfonyl)-N'-cyclohexyl-urea melting at 214°–216° C. (after crystallization from dilute acetone.

EXAMPLE 7

N-(4-[2-(1-Oxo-isoindoline-2-carboxamido)-ethyl]-benzenesulfonyl)-N'-cyclohexyl-urea 1 g of 4-[2-(1-oxo-isoindoline-2-carboxamido)-ethyl]-benzenesulfinic acid chloride (crude product, prepared by reduction of the sulfochloride with sodium sulfite and reaction of the sulfinic acid obtained with thionyl chloride) is introduced at room temperature into a solution of 0.7 g of cyclohexyl-urea in 10 ml of pyridine and the mixture is stirred for 15 minutes. Next, the reaction mixture is poured into water, the precipitate is filtered off with suction, treated with dilute ammonia and filtered again with suction. The crude product melts at 170°–172° C. 0.3 g of the compound obtained is dissolved in dimethyl formamide and aqueous potassium permanganate is added until the permanganate color is retained. The excess permanganate is destroyed with sodium sulfite, the solution is filtered and acidified with dilute hydrochloric acid. The reprecipitated compound is reprecipitated once more from very dilute ammonia and recrystallized from dilute acetone. The N-(4-[2-(1-oxo-isoindoline-2-carboxamido)-ethyl]-benzenesulfonyl)-N'-cyclohexyl-urea melts at 212°–214° C. and no depression is observed with the substance of Example 1.

EXAMPLE 8

N-(4-[2-(1-Oxo-isoindoline-2-carboxamido)-ethyl]-benzenesulfonyl)-N'-butyl-urea 3.4 g of 4-[2-(1-oxo-isoindoline-2-carboxamido)-ethyl]-benzenesulfinic acid (crude product, prepared by reduction of the sulfochloride with sodium sulfite) and 1.4 g of N-hydroxy-N'-butyl-urea are suspended in 40 ml of dioxane and a solution of 1 ml of thionyl chloride in 10 ml of dioxane is added dropwise while stirring. The mixture is then heated for 2 hours to 60° C., whereby a limpid solution is formed. The solution is poured into water, the precipitated substance is treated with dilute ammonia, filtered, acidified and the reaction product is recrystallized from dilute acetone. The N-(4-[2-(1-oxo-isoindoline-2-carboxamido)-ethyl]-benzenesulfonyl)-N'-butyl-urea obtained melts at 188°–190° C.

EXAMPLE 9

N-(4-[2-(1-Oxo-isoindoline-2-carboxamido)-ethyl]-benzenesulfonyl)-N'-butyl-urea 3 g of N-(4-[2-amino-ethyl]-benzenesulfonyl)-N'-butyl-urea (melting point 210°–212° C., prepared by saponification of N-(4-[2-acetylamino-ethyl]-benzenesulfonyl)-N'-butyl-urea with sodium hydroxide solution) are dissolved with 0.4 g of sodium hydroxide in 50 ml of water and 50 ml of acetone and, while stirring, a solution of 2 g of 1-oxo-isoindoline-2-carboxylic acid chloride (melting point 119°–121° C., prepared from 1-oxo-isoindoline sodium and phosgene) in about 50 ml of acetone is added. The temperature of the mixture increases slightly. Stirring is continued for 2 hours at room temperature, whereupon the residue is acidified with dilute hydrochloric acid. The precipitate is reprecipitated from dilute ammonia and recrystallized from dilute acetone. The N-(4-[2-(1-oxo-isoindoline-2-carboxamido)-ethyl]-benzenesulfonyl)-N'-butyl-urea melts at 188°–190° C.

EXAMPLE 10

N-(4-[2-(1-Oxo-isoindoline-2-carboxamido)-ethyl]-benzenesulfonyl)-N'-butyl-urea 4.8 g of butyl urea are dissolved in 100 ml of tetrahydrofurane and, while stirring, 1.5 g of 80% sodium hydride (in oil) are added. The mixture is heated for 3 hours to 60° C. whereupon 7.6 g of 4-[2-(1-oxo-isoindoline-2-carboxamido)-ethyl]-benzene-sulfochloride in 100 ml of tetrahydrofurane are added while cooling. The temperature is slowly raised to 60°–70° C. and stirring is continued at that temperature for 3 hours. The solvent is removed under reduced pressure, water is added to the residue, the mixture is filtered and the filtrate is acidified with dilute hydrochloric acid. After recrystallization from dilute acetone, the N-(4-[2-(1-oxo-isoindoline-2-carboxamido)-ethyl]benzenesulfonyl)-N'-butyl-urea melts at 189°–190° C.

EXAMPLE 11

N-(4-[2-(1-Oxo-isoindoline-2-carboxamido)-ethyl]-benzenesulfonyl)-N'-butyl-urea 4 g of N-(4-[2-(-1-oxo-isoindoline-2-carboxamido)ethyl]-benzenesulfonyl-urea (melting point 207°–209° C., prepared from 4-[2-(1-oxo-isoindoline-2-carboxamido)-ethyl]-benzenesulfonamide and potassium cyanate in 80% ethanol) and 0.73 g of butylamine in 100 ml of dioxane are refluxed for 1 hour. The solvent is then distilled off under reduced pressure, the residue is reprecipitated from very dilute ammonia and recrystallized from dilute acetone. The N-(4-[2-(1-oxo-isoindoline-2-carboxamido)-ethyl]-benzenesulfonyl)-N'-butyl urea obtained melts at 188° to 190° C.

EXAMPLE 12

N-(4-[2-(1-Oxo-isoindoline-2-carboxamido)-ethyl]-benzenesulfonyl)-N'-cyclohexyl-urea 3.6 g of 4-[2-(1-oxo-isoindoline-2-carboxamido)-ethyl]-benzenesulfon-amide are carefully mixed with 2.5 g of trichloroacetyl-cyclohexyl amide and 2.8 g of potassium carbonate and the mixture is heated in a bath for 1 hour at 160° C. After cooling, the reaction mixture is treated with water and hydrochloric acid, filtered off with suction and the reaction product is reprecipitated from very dilute ammonia and recrystallized from dilute acetone. The N-(4-[2-(1-oxo-isoindoline-2-carboxamido)-ethyl]-benzenesulfonyl)-N'-cyclohexyl-urea obtained melts at 214°–216° C.

What is claimed is:

1. A sulfonylurea having the formula

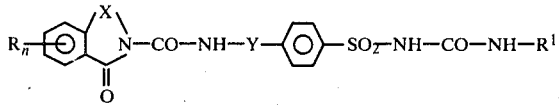

wherein n is 1 or 2, R is hydrogen, alkyl or alkoxy with 1 to 4 carbon atoms or halogen which may be identical or different when n is 2, X is —CH$_2$— or

Y is alkylene with 2 or 3 carbon atoms, and R$^1$ is alkyl with 2 to 8 carbon atoms, cycloalkyl, alkylcycloalkyl, dialkylcycloalkyl, cycloalkylalkyl, cycloalkenyl or alkylcycloalkenyl, in each case with 4 to 9 carbon atoms, methylcyclopentylmethyl, cyclohexenylmethyl, chlorocyclohexyl, methoxycyclohexyl, 2-bicyclo[2,2,1]heptyl, 2-bicyclo[2,2,1]hept-5-enyl, 2-bicyclo[2,2,1]heptylmethyl, 2-bicyclo[2,2,1]hept-5-enylmethyl, 2-bicyclo[2,2,2]octyl, nortricyclyl, adamantyl or benzyl, or a physiologically tolerated salt thereof.

2. The compound of claim 1, wherein Y is —CH$_2$—CH$_2$—.

3. The compound of claim 1, wherein X is —CH$_2$—.

4. The compound of claim 1, wherein R is hydrogen, methyl or chlorine.

5. The compound of claim 1, wherein R$^1$ is butyl, isobutyl, methylcyclopentyl, cyclohexyl or cyclopentylmethyl.

6. A sulfonylurea having the formula

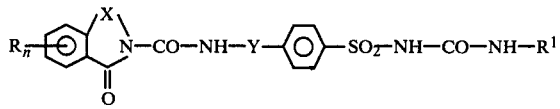

wherein n is 1 or 2, R is hydrogen, X is —CH$_2$—, Y is —CH$_2$—CH$_2$— and R$^1$ is 3-methylcyclopentyl or cyclohexyl, or a physiologically tolerated salt thereof.

7. A pharmaceutical composition for the treatment of diabetes mellitus which comprises a pharmaceutically effective amount of a sulfonylurea defined in claim 1 or a physiologically tolerated salt thereof and a pharmaceutically acceptable carrier therefor.

8. Process for lowering the blood sugar level in the treatment of diabetes which comprises administering to a patient in need thereof an effective amount of a compound as defined in claim 1.

* * * * *